United States Patent [19]

Srinivasan

[11] Patent Number: 5,021,556

[45] Date of Patent: Jun. 4, 1991

[54] METHOD OF RADIOLABELING CHELATING COMPOUNDS COMPRISING SULFUR ATOMS WITH METAL RADIONUCLIDES

[75] Inventor: Ananthachari Srinivasan, Kirkland, Wash.

[73] Assignee: NeoRx Corporation, Seattle, Wash.

[21] Appl. No.: 212,688

[22] Filed: Jul. 1, 1988

Related U.S. Application Data

[63] Continuation-in-part of Ser. No. 76,277, Jul. 22, 1987, abandoned.

[51] Int. Cl.$^5$ .................... C07F 19/00; C07F 13/00; A61K 43/00
[52] U.S. Cl. .................................. 534/10; 534/11; 534/14; 534/15; 424/1.1
[58] Field of Search .............. 534/14, 15, 10, 11; 424/1.1

[56] References Cited

U.S. PATENT DOCUMENTS

| | | | |
|---|---|---|---|
| 4,434,151 | 2/1984 | Byrne et al. | 424/1.1 |
| 4,670,545 | 6/1987 | Fritzberg et al. | 534/14 |
| 4,673,562 | 6/1987 | Davison et al. | 424/1.1 |
| 4,746,505 | 5/1988 | Jones et al. | 534/14 X |
| 4,897,255 | 1/1990 | Fritzberg et al. | 424/1.1 |
| 4,965,392 | 10/1990 | Fritzberg et al. | 424/1.1 X |

FOREIGN PATENT DOCUMENTS

| | | |
|---|---|---|
| 0173424A1 | 3/1986 | European Pat. Off. |
| 0188256A2 | 7/1986 | European Pat. Off. |

OTHER PUBLICATIONS

K. E. Baidoo, "Synthesis of Tc-99m-N$_2$S$_2$ Complexes Via the p-Methoxybenzyl Protected Thiol Ligand", *J. Nuc. Med.*, vol. 27, No. 6, Jun. 1986, p. 1050.
F. W. Greene, "Protective Groups in Organic Synthesis", John Wiley and Sons, New York, New York, pp. 204-209 and 216-217 (1981).
A. Davison et al, "A New Class of Oxotechnetium(5+) Chelate Complexes Containing a TcON$_2$S$_2$ Core", *Inorganic Chemistry*, vol. 20, No. 6 (Jun. 1981).
A. R. Fritzberg et al., "Synthesis and Biological Evaluation of Tc-99m N,N'-Bis(Mercaptoacetyl)-2,3-Diaminopropanoate: A Potention Replacement for [$^{131}$I]o-iodohippurate", *J. Nucl. Med.*, 23, pp. 592-598 (1982), [Fritzberg et al. I].
A. R. Fritzberg et al., "Chemical and Biological Studies of Tc-99m N,N'-Bis(Mercaptoacetamido)-Ethylenediamine: A Potential Replacement of I-131 Iodohippurate", *J. Nucl. Med.*, 22, pp. 258-263 (1981), [Fritzberg et al. II].
A. R. Fritzberg et al., "Synthesis and Characterization of Re and Tc Complexes of N$_2$S$_2$ and N$_3$S Ligands", Sixth International Symposium on Radiopharmaceutical Chemistry, p. 95, Boston, 1986, ]Fritzberg et al. III].
S. Kasina et al., "Application of Diamide Dimercaptide N$_2$S$_2$ Bifunctional Chelating Agents for 99mTc-Labeling of Proteins", *6th International Symp. on Radiopharmaceutical Chem.*, Boston, 1986.

*Primary Examiner*—Robert L. Stoll
*Assistant Examiner*—John M. Covert
*Attorney, Agent, or Firm*—Kathryn A. Seese

[57] ABSTRACT

Chelating compounds which comprise one or more sulfur atoms and are to be radiolabeled with metal radionuclides to form the corresponding chelates are disclosed. The chelating compounds comprise thioacetal or hemithioacetal sulfur protecting groups which are displaced during the radiolabeling reaction, which is conducted at acidic pH, such that bonds form between said sulfur atoms and said radionuclide. The resulting metal radionuclide chelates have diagnostic and therapeutic medical uses.

20 Claims, No Drawings

METHOD OF RADIOLABELING CHELATING COMPOUNDS COMPRISING SULFUR ATOMS WITH METAL RADIONUCLIDES

CROSS-REFERENCE TO RELATED APPLICATIONS

This application is a continuation-in-part of application Ser. No. 076,277, filed July 22, 1987, now abandoned, which is hereby incorporated by reference in its entirety.

TECHNICAL FIELD OF THE INVENTION

The present invention relates to methods for radiolabeling chelating compounds comprising sulfur atoms with metal radionuclides. The resulting chelates have diagnostic and therapeutic medical uses.

BACKGROUND OF THE INVENTION

Radiolabeled compounds are important tools in medical diagnosis and treatment. Such compounds are employed in a variety of techniques, including the diagnosis of deep venous thrombi; the study of lymph node pathology; and the detection, staging, and treatment of neoplasms. A number of these compounds employ metal radionuclides such as Technetium-99m. Radiolabeling of small molecules of various chemical structures to form metal radionuclide chelates has been described. Certain of these chelates are administered per se for medical purposes (e.g., diagnostic imaging). Other chelating compounds may be bound in vitro to proteins such as antibodies, then radiolabeled to form metal radionuclide chelate-protein conjugates, in efforts to deliver the radionuclide to a specific target site within a mammal. Alternatively, the chelate may be formed prior to attachment to a protein to form the conjugate.

Several such chelates comprise a metal radionuclide bound through covalent bonds to atoms of the chelating compound generally chosen from sulfur, nitrogen, or oxygen atoms, occasionally phosphorus atoms, or combinations thereof. In the case of chelating compounds comprising one or more sulfur atoms, various chemical groups generally are attached to the sulfur atoms as sulfur protective groups. These groups prevent undesired reactions of the sulfur atoms during synthesis of the chelating compounds and prior to the radiolabeling step. Radiolabeling of such chelating compounds has been accomplished by various methods which often have involved multistep procedures and/or separate steps for removal of the sulfur-protective groups prior to the radiolabeling reaction.

In view of the efforts underway to develop metal radionuclide chelates for medical use, a need for simple, efficient methods of radiolabeling chelating compounds to form the corresponding chelates is needed.

Publications of interest include: Khaw et al., *J. Nucl. Med.* (1982) 23:1011; Rhodes, B. A., *Sem. Nucl. Med.* (1974) 4:281; Davidson et al., *Inorg. Chem.* (1981) 20:1629; Byrne and Tolman, *J. Nucl. Med.* (1983) 24:126; Fritzberg et al., *J. Nucl. Med.* (1982) 23:592; Fritzberg et al., ibid. (1981) 22:258; Fritzberg et al., ibid. (1982) 23:17; U.S. Pat. Nos. 4,440,690, and 4,673,562.

SUMMARY OF THE INVENTION

The present invention provides a method of radiolabeling a chelating compound comprising one or more sulfur atoms with a metal radionuclide to form a chelate, wherein said sulfur atoms are bonded to said metal radionuclide in the chelate. The method is especially advantageous when the chelating compound comprises one or more base labile groups. The method comprises attaching a thioacetal or hemithioacetal sulfur protective group to each of said sulfur atoms, then reacting the resulting chelating compound comprising one or more of said sulfur protective groups with the metal radionuclide under conditions of acidic pH, thereby forming the chelate. The metal radionuclide may be an isotope of technetium, rhenium, lead, palladium, bismuth, or copper, among others.

The sulfur protective group, when taken together with two of said sulfur atoms of the chelating compound, may be a thioacetal sulfur protective group represented by the formula:

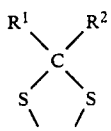

wherein $R^1$ and $R^2$ are the same or different and are selected from the group consisting of hydrogen; lower alkyl groups; and an aromatic ring having an electron donating group bonded directly to the aromatic ring.

The sulfur protective group, when taken together with one of said sulfur atoms of the chelating compound, may be a hemithioacetal sulfur protective group of the formula:

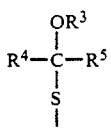

wherein $R^3$ and $R^4$ each represent a lower alkyl group, and $R^5$ represents hydrogen or a lower alkyl group. Alternatively, $R^3$ and $R^4$ may be taken together with the carbon atom and the oxygen atom shown in the formula to define a non-aromatic ring, and $R_5$ represents hydrogen or a lower alkyl group.

Also provided by the present invention are chelating compounds to be radiolabeled with metal radionuclides, comprising one or more thioacetal or hemithioacetal sulfur protective groups. The chelating compounds additionally may comprise one or more base labile groups.

DETAILED DESCRIPTION OF THE INVENTION

The present invention provides a method of radiolabeling chelating compounds comprising one or more sulfur atoms, with a metal radionuclide. The sulfur atoms participate in binding of the radionuclide to form the corresponding chelate (i.e., covalent bonds form between the metal radionuclide and the sulfur atoms during the radiolabeling reaction). Covalent bonds between the metal radionuclide and other atoms of the chelating compound, generally oxygen and/or nitrogen atoms, also may form. These nitrogen, oxygen, and sulfur atoms are referred to as "donor atoms". The total number of bonds which form between atoms of the chelating compound and the radionuclide preferably is four, to yield chelates in which the radionuclide is bound most stably.

The method of the invention involves the use of hemithioacetal or thioacetal sulfur protective groups on one or more sulfur atoms of a chelating compound to be radiolabeled with a metal radionuclide to form a chelate. These sulfur-protective groups are displaced during the radiolabeling reaction, conducted at acidic pH, in what is believed to be metal-assisted acid cleavage; and covalent bonds form between the sulfur atoms and the metal radionuclide.

The present invention provides a method of producing a radionuclide metal chelate, comprising reacting a radionuclide metal with a chelating compound under conditions of acidic pH, thereby producing said radionuclide metal chelate, wherein said chelating compound comprises one or more sulfur donor atoms attached to a protecting group, and said protecting group, when taken together with the one or more sulfur donor atoms attached thereto, is a hemithioacetal group or a thioacetal group.

Advantages of the present method include the fact that a separate step for removal of the sulfur-protective groups is not necessary. The radiolabeling procedure thus is simplified, which is especially advantageous when the chelating compounds are to be radiolabeled in a hospital laboratory shortly before use. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. In general, such groups include Michael acceptors (e.g., esters or maleimides), and isothiocyanates, among others. Certain of such groups may be present on the chelating compound for reaction with proteins to bind the corresponding chelate to the protein (see, for example, European Patent Application, publication number 188,256). When radiolabeling is conducted at basic pH (especially at a pH above 9 or 10), such groups may be substantially hydrolyzed and must be generated (or regenerated) after the radiolabeling step. Generation of the ester group generally involves a multistep procedure (e.g., by using a carbodiimide and a hydroxylic compound). These extra steps, and the need to remove carbodiimide and phenolic compounds (which may damage the protein when it is added) from the reaction mixture, are avoided when thioacetal and hemithioacetal protecting groups are used. Chelating compounds comprising esters thus are ready for conjugation to proteins immediately after radiolabeling without any esterification steps.

The present invention thus provides a method for radiolabeling chelating compounds comprising sulfur atoms which is simple and efficient, and avoids additional chemical reaction steps associated with certain other procedures. The method of the invention thus is especially advantageous in clinical or hospital settings and is well suited for use in conjunction with diagnostic or therapeutic kits comprising such chelating compounds, whereby chelates can be prepared by the relatively simple radiolabeling procedure.

In addition, when certain chelates are to be conjugated to targeting molecules such as proteins, these chelates often are bonded to the protein prior to the radiolabeling step so that a base labile group on the chelating compound which reacts with the protein to form the bond thereto (e.g., an ester group) is not exposed to the basic pH conditions during the radiolabeling step. Use of the hemithioacetal or thioacetal sulfur protective groups makes preparation of the chelate prior to conjugation to the protein possible in these situations.

Chelating compounds comprising thioacetal or hemithioacetal sulfur-protective groups also are provided by the present invention. The chelating compounds of the present invention comprise sulfur-protective groups which, when taken together with the sulfur atoms to be protected, represent thioacetals or hemithioacetals. The chelating compounds are capable of binding a metal (e.g., a radionuclide metal) to form a chelate, and comprise one or more sulfur donor atoms attached to a protecting group to form a thioacetal or hemithioacetal group. Thioacetals and hemithioacetals which may be used in the present invention include those groups which effectively maintain the sulfurs in a nonreactive state until the radiolabeling step, at which time the protective groups are displaced in the presence of the metallic radioisotope under acidic conditions. In general, the hemithioacetal S-protecting groups are somewhat more acid labile in the radiolabeling reaction than the thioacetal groups, and therefore are generally preferred.

When a thioacetal group is used, a single protecting group protects two sulfur atoms present on a chelating compound. The thioacetal groups contain a carbon atom directly bonded to two sulfur atoms, i.e.,

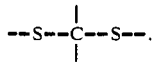

Suitable thioacetals generally have the following formula in which the two sulfur atoms shown are the sulfur atoms of the chelating compound:

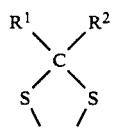

wherein $R^1$ and $R^2$ are the same or different and are selected from hydrogen; lower alkyl groups (preferably of from one to three carbon atoms, most preferably a methyl group); or an aromatic (phenyl) ring with an electron donating group (e.g., a methoxy, ethoxy, or hydroxy group with methoxy being preferred) bonded directly to the ring, preferably in the para position. When either $R^1$ or $R^2$ comprises a phenyl ring, the other preferably is hydrogen so that the desired degree of water solubility is retained.

Examples of suitable thioacetals include but are not limited to p-anisylidine:

and acetonyl:

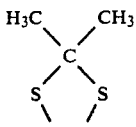

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

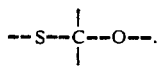

Suitable hemithioacetals include but are not limited to those having the following formulae, wherein the sulfur atom is a sulfur atom of the chelating compound, and a separate protecting group is attached to each of the sulfur atoms on the chelating compound:

—S—CH$_2$—O—CH$_2$—CH(CH$_3$)

—SCH$_2$—OCH$_3$

—S—CH$_2$—O—(CH$_2$)$_2$—OCH$_3$

Preferred hemithioacetals generally are of the following formula, wherein the sulfur atom is a sulfur atom of the chelating compound, and a separate protecting group is attached to each of the sulfur atoms on the chelating compound:

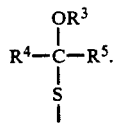

wherein R$^3$ is a lower alkyl group, preferably of from two to five carbon atoms, and R$^4$ is a lower alkyl group, preferably of from one to three carbon atoms. Alternatively, R$^3$ and R$^4$ may be taken together with the carbon atom and the oxygen atom shown in the formula to define a nonaromatic ring, preferably comprising from three to seven carbon atoms in addition to the carbon and oxygen atoms shown in the formula. R$^5$ represents hydrogen or a lower alkyl group wherein the alkyl group preferably is of from one to three carbon atoms.

Examples of such preferred hemithioacetals include, but are not limited to:

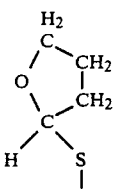

Tetrahydrofuranyl

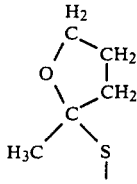

2-methyl tetrahydrofuranyl

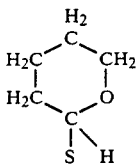

Tetrahydropyranyl

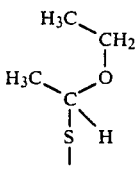

ethoxyethyl

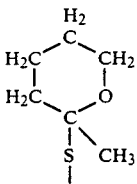

2-methyl tetrahydropyranyl

In general, the above-described thioacetals and hemithioacetals should not comprise long hydrocarbon chains. Such chains would diminish the desired water solubility of the chelating compounds of the invention and may decrease the ease of synthesis thereof. Water solubility is desirable in certain situations, such as when the chelating compound is to be bound to a protein. Such a reaction should be conducted in a reaction mixture which is at least partially aqueous, since a totally organic reaction mixture may denature or otherwise damage the protein. Conducting he radiolabeling reaction in an aqueous or mixed organic/aqueous solvent may be preferable as well, since certain organic solvents are unpleasant to work with and/or toxic.

Other hemithioacetal sulfur-protecting groups may be derived from sugars such as monosaccharides. In one embodiment of the invention, the sulfur protecting group is a monosaccharide comprising five or six carbon atoms, or a derivative thereof. The use of these sulfur protecting groups enhances the water solubility of the chelating compound.

A chelating compound may be synthesized to comprise a monosaccharide protecting group on one or more sulfur donor atoms of the chelating compound. Alternatively, a sugar molecule (e.g., a commercially available monosaccharide) may be attached to a chelating compound as a sulfur protecting group through any suitable chemical reaction. The sugar molecule may be derivatized to attach various chemically reactive groups thereto, so that the sugar can be attached to a sulfur donor atom in a chelating compound.

Examples of some of the many monosaccharides comprising five or six carbon atoms that can be used as sulfur protecting groups are D-glucose, D-galactose, L-rhamnose, D-xylose, and derivatives thereof. Procedures for producing chelating compounds having one or more monosaccharide sulfur protecting groups include the procedures presented in example 5 below.

The enhanced water solubility of the sugar sulfur protecting groups is especially beneficial when the chelating compound is to be attached to a protein such as an antibody prior to the radiolabeling reaction. Water solubility of the chelating compound is desirable so that the compound can be reacted with a protein in an aqueous reaction mixture.

It is to be noted that in certain circumstances, when a chelating compound comprises more than one sulfur atom, a protective group other than the sulfur protective groups of the present invention may be attached to one of sulfur atoms, as long as the other sulfur atom(s) have thioacetal or hemithioacetal protecting groups of the invention attached thereto. Once three bonds to the radionuclide have formed during the radiolabeling reaction of the invention, the tendency of the radionuclide to form four bonds to achieve maximum stability may result in displacement of the non-hemithioacetal/thioacetal protective group from the fourth (sulfur) atom.

The chelating compounds of the present invention are radiolabeled with a metal radionuclide to form the corresponding chelate. A variety of metals may be employed as the radionuclide. These radionuclide metals include, but are not limited to, radioisotopes of copper (e.g., $^{67}$Cu and $^{64}$Cu); technetium (e.g., $^{99m}$Tc); rhenium (e.g., $^{186}$Re and $^{188}$Re); lead (e.g., $^{212}$Pb); bismuth (e.g., $^{212}$Bi); and palladium (e.g., $^{109}$Pd). Methods for preparing these isotopes are known. Molybdenum/technetium generators for producing $^{99m}$Tc are commercially available. Procedures for producing $^{186}$Re include the procedures described by Deutsch et al, (*Nucl. Med. Biol.* Vol. 13:4:465-477, 1986) and Vanderheyden et al, (*Inorganic Chemistry*, Vol. 24:1666-1673, 1985), and methods for production of $^{188}$Re have been described by Blachot et al (*Intl. J. of Applied Radiation and Isotopes* Vol. 20:467-470, 1969) and by Klofutar et al (*J. of Radioanalytical Chem.*, Vol. 5:3-10, 1970). Production of $^{109}$Pd is described in Fawwaz et al., *J. Nucl. Med.* (1984), 25:796. Production of $^{212}$Pb and $^{212}$Bi is described in Gansow et al., *Amer. Chem. Soc. Symp. Ser.* (1984), 241:215-217 and Kozah et al., *Proc. Nat'l Acad. Sci.* USA (January 1986) 83:474-478. Chelates comprising technetium have diagnostic use and are especially suitable for administration followed by scanning the patient at an appropriate time with a gamma camera to image the localization of the radionuclide in the patient. The other radionuclides have use as therapeutic agents (e.g., for destruction of tumor tissue).

The thioacetal and hemithioacetal groups of the invention may be attached to the sulfur atom(s) of any chelating compound having one or more sulfur atoms which participate in binding a metal radionuclide in the corresponding chelate. Atoms that form bonds to the metal to form the chelate are called donor atom. Since the chelating compound will be radiolabeled at an acidic pH, the compound should not comprise acid labile functional groups which are essential to the use of the compound. These compounds may have a variety of chemical structures and are synthesized by known procedures. For example, chelating compounds having various structures which comprise sulfur atoms which participate in binding a metal radionuclide, and the synthesis thereof, are described in U.S. Pat. Nos. 4,440,690; 4,670,545; and 4,673,562, as well as European Patent Application publication number 188,256, and Schneider et al., *J. Nucl. Med.*, 25:223-229 (1984).

In one embodiment of the invention, the chelating compound comprises a total of at least four donor atoms selected from nitrogen and sulfur donor atoms, with at least one sulfur donor atom. One example of such a chelating compound is an "N$_2$S$_2$" chelating compound that comprises two nitrogen donor atoms and two sulfur donor atoms, such as a compound of the following formula:

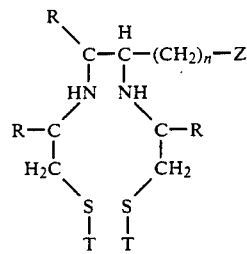

wherein n is from 1 to about 4 (preferably 2); Z represents a protein conjugation group or a targeting molecule; each R independently is selected from =O and H$_2$; and T represents a sulfur protecting group. Each T may represent one of the above-described hemithioacetal protecting groups (when taken together with the sulfur atom.) Alternatively, both T symbols may represent a single protecting group attached to both sulfur donor atoms to form one of the above-described thioacetal groups. In one embodiment of the invention, each T represents a protecting group derived from a monosaccharide, such as those described in Example 5 below.

Protein conjugation group Z is a group that will react with a functional group on a targeting molecule to bind the chelating compound (or a chelate prepared therefrom) to the targeting molecule. A targeting molecule is capable of localizing at a desired target site in vivo, thus delivering the radionuclide metal chelate to the target site. Targeting molecules include proteins such as antibodies, hormones, enzymes, biologic response modifiers, and many other molecules, with the choice being dependent on the particular target site of interest. One example of a targeting molecule is a monoclonal antibody that binds to a tumor target site in vivo.

Protein targeting molecules contain (or may be derivatized to contain) a number of functional groups (e.g. free amines, carboxylates, and sulfhydryls) that may react with a protein conjugation group Z on a chelating compound or chelate. In one embodiment of the invention, Z represents a base labile protein conjugation group such as an ester (e.g. a tetrafluorophenyl ester), an isothiocyanate, a maleimide, or another michael-type acceptor group.

The $N_2S_2$ chelating compound may be radiolabeled before or after attachment to the targeting molecule to produce a radionuclide metal chelate of the formula:

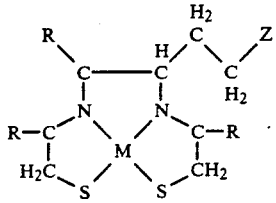

wherein M represents a radionuclide metal or an oxide thereof.

Another example of a chelating compound of the present invention is an "$N_3S$" compound comprising three nitrogen donor atoms and one sulfur donor atom, such as a compound of the following formula:

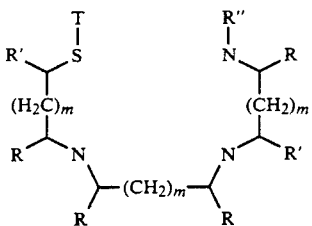

wherein:

T is a protecting group that, together with the sulfur donor atom to which it is attached, defines a hemithioacetal group;

each R independently represents $H_2$ or $=O$;

each R' independently represents a substituent selected from the group consisting of hydrogen, a non-alkyl side chain of an amino acid other than cysteine, alkyl, geminal dialkyl, and $-(CH_2)n^{-Z}$;

Z represents $-COOH$, a protein conjugation group, or a targeting molecule;

m represents 0 or 1, with the proviso that at most one m represents 1;

n is an integer of from 1 to about 4; and

R" is hydrogen; $-(CH_2)n^{-Z}$; or an alkyl group having one or more polar groups substituted thereon;

wherein the compound comprises at least one $-(CH_2)n^{-Z}$ substituent.

The protein conjugation group and targeting molecule are as described for the $N_2S_2$ compound. In one embodiment of the invention, T represents a protecting group derived from a monosaccharide, such one of those described in Example 5 below. The protein conjugation group Z may be a base labile group, as described above.

Radiolabeling of this $N_3S$ chelating compound in accordance with the invention produces a radionuclide metal chelate of the following formula:

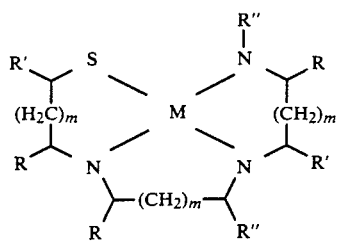

wherein M represents a radionuclide metal or oxide thereof.

Methods for synthesizing various $N_3S$ chelating compounds are known. See, for example, European patent application publication number 173, 424.

Other chelating compounds may have different combinations of donor atoms. Such compounds include $N_2S_4$, $N_2S_3$, and $N_3S_3$ chelating compounds, among others.

In accordance with the present invention, the chelating compounds of the invention, which comprise hemithioacetal or thioacetal sulfur protective groups, are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the chelating compounds of the invention.

In the case of technetium and rhenium, being in "chelatable form" requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}TcO_4^-$ which is in the +7 oxidation level) or sodium perrhenate (i.e., $^{188}ReO_4^-$, $^{186}ReO_4^-$) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene diphosphonate, glyceric acid, glycolic acid, mannitol, oxalic acid, malonic acid, succinic acid, bicine, N,N'-bis(2-hydroxy ethyl) ethylene diamine, citric acid, ascorbic acid and gentisic acid. Good results are obtained using gluconic acid or glucoheptonic acid as the Tc-complexing agent and citric acid for rhenium. When the radionuclide in the form of such an exchange complex is reacted with the chelating compounds of the invention, the radionuclide will transfer to these compounds which bind the radionuclide more strongly to form chelates of the invention. Heating is often required to promote transfer of the radionuclide. Radionuclides in the form of such complexes also are considered to be in "chelatable form" for purposes of the present invention.

Chelates of $^{212}$Pb, $^{212}$Bi, and $^{109}$Pd may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation (i.e., in chelatable form).

The specific radiolabeling reaction conditions may vary somewhat according to the particular radionuclide and chelating compound involved. In one embodiment of the invention, a $^{99m}$Tc chelate is prepared as follows.

An aqueous solution comprising a reducing agent and a complexing agent is prepared. Good results are achieved by combining stannous chloride dihydrate (comprising the stannous ion reducing agent) and sodium gluconate (a complexing agent) to form a stannous gluconate complex. In one embodiment of the invention, the stannous gluconate complex is provided in dry solid form. Optionally, one or more stabilizer compounds may be added to the stannous gluconate complex. Many such stabilizer compounds are known and are discussed below. For example, gentisic acid may be added to a container of the stannous gluconate complex to stabilize (minimize oxidation of) the stannous ion reducing agent, and the resulting mixture may be provided in dry solid form or as a lyophilized preparation. A filler compound advantageously is added prior to lyophilization, as described below. For example, lactose may be added as a filler compound in an amount effective in facilitating lyophilization. An acceptable ratio of stannous chloride dihydrate to sodium gluconate (by weight) is from about 1:10 to about 1:100, preferably from about 1:25 to about 1:70, most preferably about 1:41.6.

Sodium pertechnetate is combined with the reducing agent and complexing agent. When the sodium pertechnetate is added to stannous gluconate, the radioisotope is effectively reduced to a lower oxidation state and complexed with gluconate to form an exchange complex. The stannous gluconate and pertechnetate may be combined in various ways. In one embodiment of the invention, sterile water is added to a vial containing a stannous gluconate preparation in dry solid form. A portion of the resulting solution is combined with about 0.75 mL sodium pertechnetate (about 75 to 100 uCi). In another embodiment of the invention, sodium pertechnetate (about 1 mL) is added directly to a lyophilized preparation comprising stannous gluconate, gentisic acid as a stabilizer, and lactose as a filler compound. In either case, the reaction mixture is incubated at about 25° C. to about 50° C., preferably at about 25° C. to about 37° C. for a minimum of 10 minutes. Incubation for 10 minutes generally gives sufficient yields of the desired technetium exchange complex (e.g., technetium gluconate) while minimizing the formation of insoluble technetium dioxide, which may increase with increased incubation time.

A chelating compound of the invention, comprising two nitrogen atoms and two sulfur atoms having thioacetal or hemithioacetal S-protecting groups attached thereto, as described above, is added to an organic solvent effective in dissolving the chelating compound and suitable for the exchange reaction that follows. Suitable solvents should be nontoxic in mammals and inert toward the reactants in the reaction mixture. Organic solvents which may be used include acetonitrile, ethyl acetate, and methylethyl ketone. When the resulting chelate is to be injected into humans, however, suitable organic solvents include, but are not limited to, alcohols such as ethanol, butanol, t-butyl alcohol and propanol, and polar aprotic solvents such as DMSO and dimethylformamide. The choice of solvent may vary according to the particular chelating agent. A preferred organic solvent is isopropyl alcohol. The concentration of the organic solvent in the following Tc-labeling exchange reaction mixture should be between about 10% and about 30%, preferably between about 15% and about 25%.

The solution comprising the chelating agent in the organic solvent is then acidified to a pH of about 2.0 to about 5.0, preferably 2.8 to 3.3. At these acidic pH conditions, the formation of insoluble $TcO_2$ will be minimized, and, as explained above, hemithioacetal and thioacetal sulfur-protecting groups will be displaced by a metal-assisted acid cleavage during the technetium labeling exchange reaction to form the corresponding technetium chelate compound. Suitable acids are added in amounts sufficient to displace the sulfur-protective groups in the presence of the metal radionuclide (i.e., in amounts sufficient to adjust the reaction mixture to the above-described pH values range). Suitable acids include, but are not limited to, phosphoric acid, sulfuric acid, nitric acid, glacial acetic acid, hydrochloric acid and combinations thereof. Also included are solutions comprising such acids and buffers (e.g., acetate and phosphate buffers). Good results have been achieved using a solution comprising glacial acetic acid and 0.2 N HCl at a ratio of 2:14.

The acidified chelating compound solution is combined with the previously prepared technetium exchange complex solution, to form the corresponding chelate compound, such that about 100 ug to about 150 ug, preferably about 135 ug of chelating compound is combined with the Tc-gluconate complex prepared from the 75 to about 100 mCi of technetium as described above. The reaction mixture is heated to between about 50° C. and 100° C. for from about 5 minutes to about 45 minutes. Good results have been achieved by heating at about 75° C. for about 15+2 minutes. Heating the reaction mixture accelerates the exchange reaction to form the $N_2S_2$ chelate. Upon completion of the reaction, the mixture is transferred immediately to a 0° C. ice bath for a minimum of 2 minutes to stop the reaction.

In another embodiment of the invention, a chelate comprising either $^{188}$Re or $^{186}$Re may be prepared. Perrhenate (the $ReO_4^-$ form of the $^{186}$Re or $^{188}$Re isotope) is reacted with a reducing agent and a complexing agent. Good results are achieved by combining citric acid (a complexing agent) with stannous chloride (a reducing agent) in a single container (in which a stannous citrate complex is believed to form) and adding the perrhenate thereto. An acceptable ratio of stannous chloride to citric acid (by weight) generally is from about 1:10 to about 1:5500, preferably from about 1:20 to about 1:200, most preferably about 1:100.

One or more stabilizer compounds may be added to the stannous citrate complex. Many such stabilizer compounds are known. See, for example, U.S. Pat. Nos. 4,440,738 and 4,510,125. Advantageously, gentisic acid is added to the stannous citrate to stabilize (e.g., to prevent oxidation of) the stannous ion. The stabilizer is added to a solution comprising the stannous chloride reducing agent (and the complexing agent) in an amount effective in stabilizing the stannous ion such that the shelf life (stability) of the stannous ion is increased. The solution may be lyophilized and provided in the kit as a lyophilized powder.

When the stannous citrate solution is to be lyophilized, a "filler compound" may be added to the solution to provide bulk or mass and to aid in the lyophilization process. Good results have been achieved using lactose as the filler compound.

In one particular embodiment of the invention, an aqueous solution of stannous citrate was prepared by combining about 75 mg citric acid with about 750 ug stannous chloride. About 250 ug gentisic acid was added. When 50 ug of gentisic acid was added, the stabilizing effect was not as efficient, whereas 1 mg gentisic acid was found to be too large an amount, having a negative affect on yields. About 100 mg lactose (a preferred amount) is then added to the preparation, although about 20 mg is generally adequate. The final solution (about 2 mLs volume) then is lyophilized.

Perrhenate is added to the stannous citrate preparation. Perrhenate can be introduced into the preparation as an aqueous solution of the sodium salt (e.g., eluted from a rhenium generator). Perrhenate is incubated with a solution comprising a reducing agent and a complexing agent. The reaction mixture is incubated at about 25° C. to about 50° C., preferably at about 25° to 37° C., for a minimum of 10 minutes. Incubation for 10 minutes generally gives sufficient yields of the desired rhenium exchange complex (e.g., rhenium-citrate), while minimizing the formation of insoluble rhenium dioxide.

A chelating compound of the invention comprising two nitrogen atoms and two sulfur atoms having thioacetal or hemithioacetal sulfur-protecting groups attached thereto, as described above, is dissolved in an organic solvent effective in dissolving the chelating compound and suitable for the exchange reaction that follows. Suitable solvents are as described above.

The solution comprising the chelating compound is combined with the rhenium exchange complex solution prepared above to form the corresponding rhenium chelate compound. The reaction advantageously is conducted at a pH of from about 1.5 to about 5.0, preferably from about 1.7 to about 2.0. At these acidic pH conditions, the formation of insoluble $ReO_2$ will be minimized; and as explained above, hemithioacetal and thioacetal sulfur- protecting groups will be displaced by a metal-assisted acid cleavage during the rhenium labeling exchange reaction to form the corresponding rhenium chelate compound. If adjustment of the pH of the reaction mixture is necessary, suitable acids may be added in amounts sufficient to displace the sulfur-protective groups in the presence of the metal radionuclide (i.e., in amounts sufficient to adjust the reaction mixture to the above-described pH values range). Suitable acids include but are not limited to phosphoric acid, sulfuric acid, nitric acid, glacial acetic acid, hydrochloric acid, and combinations thereof. Also included are solutions comprising such acids and buffers (e.g., acetate and phosphate buffers).

The reaction mixture is heated between about 50° C. and 100° C. for from about 5 to about 45 minutes. Good results have been achieved by heating at about 75° C. for about 10 minutes. Upon completion of the reaction, the mixture is transferred immediately to a 0° C. ice bath for a minimum of 2 minutes to stop the reaction and minimize the hydrolysis of the ester group.

When the perrhenate was added in a relatively large volume (e.g., about 3 mLs as an eluate from a generator), the chelate may be purified from the chelation reaction mixture using a preparative reversed phase column. Suitable columns include but are not limited to Baker C18 and C8 columns. The desired chelate is retained by the column packing material, while most impurities (e.g., starting reagents such as citric acid, gentisic acid, stannous chloride, and lactose) may be washed off the column. Good results have been achieved by washing the column (after sample loading) several times with water, then several times with a 2% to 20% ethanol/phosphate buffer solution. The column then is dried, and the chelate compound is eluted with an organic solvent, preferably $CH_3CN$, that can be dried off under mild conditions. Usually, a flow of nitrogen dispensed through needles evaporates all the solvent, leaving a white residue in the elute vial.

The following examples are presented to illustrate certain embodiments of the present invention and are not intended to limit the scope of the claims presented below. One skilled in the art will recognize variations which fall within the scope of the present invention.

EXAMPLE 1

Synthesis of Chelating Compounds of the Invention

Various hemithioacetal and thioacetal sulfur protecting groups are attached to the sulfur atoms of chelating compounds in the synthesis procedures presented below.

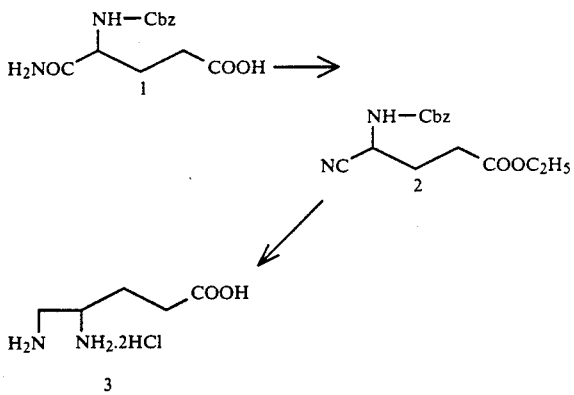

Diaminopentanoic Acid.

N-carbobenzyloxyisoglutamine was prepared according to the procedure of R. Struka and M. Zaoral. *Collection of Czechoslav. Chem. Comm.* (1977) 42:560.

N-Carbobenzyloxyisoglutamine Ethyl Ester (1)

A stirred suspension of carbobenzyloxyisoglutamine (28 g, 100 mmol) and p-toluenesulfonic acid monohydrate (1.9 g, 10 mmol) in 560 mL of absolute ethanol was gently refluxed for 12-14 hours or until TLC (1:5:94 $HOAc/H_2/CH_3CN$) indicated that the reaction was complete.

The reaction mixture was concentrated in vacuo and recrystallized from ethyl acetate/hexane to give a white solid: mp 144°-145° C.

N-Carbobenzyloxy-α-cyano-α-aminobutyric Acid Ethyl Ester (2)

To a stirred suspension of Cbz-isoglutamine ethyl ester (15.42 g, 50 mmol) and pyridine (8.48 mL, 105 mmol) in 360 mL of anhydrous THF at 0° C. was added dropwise a solution of trifluoroacetic anhydride (7.77 mL, 55 mmol) in 40 mL of THF, at such a rate to maintain a temperature of 0°–5° C. for 1–2 hours or until reaction was complete as evidenced by TLC (5% $H_2O$/94% $CH_3CN$/1% HOAc; $Cu(OAc)_2$ stain.)

The reaction mixture was concentrated in vacuo to a clear oil. The oil was taken up in ethyl acetate, washed twice with dilute aqueous HCl, once with water, once with brine, and dried over $Na_2SO_4$. The mixture was filtered and concentrated in vacuo to a clear oil. Recrystallization from cold ethanol/water gave 11.90 g (82%) of white needles: m.p. 61°–62° C.

4,5-Diaminopentanoic Acid Dihydrogen Chloride (3)

A 500 mL Parr Shaker bottle was charged with 3.0 g of N-carbobenzyloxy-cyano-amino-butyric acid ethyl ester, 500 mg of $PtO_2$ catalyst (Aldrich), 80 mL of EtOH and 80 mL of 6 N HCl. The mixture was shaken for 16 hours under 50–60 psi $H_2$ pressure. The mixture was filtered and concentrated. The resulting oily residue was dissolved in 150 mL of 6 N HCl and heated at 70° C. for 4 hours. The mixture was concentrated in vacuo, and to the resulting syrup was added 100 mL of EtOH. The mixture was allowed to stand in the refrigerator, and the resulting solid was collected by filtration to yield approximately 2 g of 3 as a white powder.

S-(1-ethoxyethyl)mercaptoacetic acid (5a)

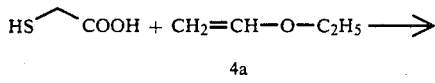

4a

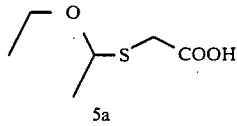

5a

A solution of mercaptoacetic acid (17.4 mL, 250 mmol) in 125 mL of dichloromethane containing p-toluenesulfonic acid monohydrate (0.24 g, 1.26 mmol) was cooled to −18° to −25° C. with stirring. Ethyl vinyl ether (23.9 mL, 250 mmol) in 125 mL of dichloromethane was added dropwise to the cold solution over a period of 90 minutes. The stirring was continued for an additional 30 minutes with the temperature maintained in the −18° to −25° C. range. Then 200 mL of pH=7 phosphate buffer was added, and the reaction mixture was allowed to warm with stirring for 10 to 15 minutes. The mixture was then poured into a flask containing 900 mL of ethyl acetate and 200 mL of water. Layers were separated and the aqueous portion extracted twice with ethyl acetate. The organic layers were combined, washed with brine and dried (MgSO$_4$). Removal of the solvent left 31.4 g of S-(1-ethoxyethyl)mercaptoacetic acid 4 as a colorless oil (77% yield): $^1$H NMR (CDCl$_3$) 1.15(t,J=7.0 Hz,3H), 1.52(d,J=6.4 Hz,3H), 3.36(s,2H), 3.60(m,2H), 4.84(q,J=6.4 Hz,1H), 11.65(s,1H). The material was used without further purification.

In similar reactions, mercaptoacetic acid was reacted with 4b and 4c to give 5b and 5c.

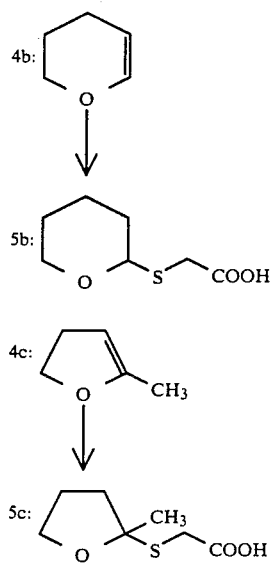

S-(Tetrahydropyranyl)mercaptoacetic acid

A solution of mercaptoacetic acid (1.4 mL, 20.0 mmol) in 3,4-dihydro-2H-pyran was cooled to 0° C. with stirring. A catalytic amount (20 mg) of p-toluenesulfonic acid monohydrate was cautiously added, and the mixture was allowed to stir at 0° C. for 30 minutes, then to room temperature for 1 hour. The excess 3,4-dihydro-2H-pyran was removed in vacuo to leave an oily residue. The residue was dissolved in tetrahydrofuran containing 2 mL of 1.0 N aqueous HCl and allowed to stir at room temperature for 20 minutes. The tetrahydrofuran was evaporated, and the residue was dissolved in ethyl acetate. The ethyl acetate solution was extracted with 5% aqueous sodium bicarbonate. The bicarbonate extracts were combined and washed with ethyl acetate. Fresh ethyl acetate was added to bicarbonate extracts, and the aqueous layer was acidified to pH 1 with 1.0 N aqueous HCl. The layers were separated, and the aqueous portion was extracted twice with ethyl acetate. The organic layers were combined and dried (MgSO$_4$). Removal of the solvent afforded 3.28 g of 5b as a viscous oil (93% yield): $^1$H NMR(CDCl$_3$) 1.68(b,6H), 3.34(m,2H), 3.62(m,1H), 3.90(m,1H), 5.05(b,1H), 11.5(s,1H). The material was used without further purification.

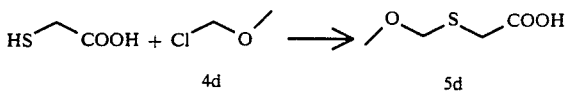

S-Methoxymethyl-mercaptoacetic acid (5d)

To a solution of 1.40 mL (1.84 g, 20 mmol) mercaptoacetic acid and 8.36 mL (6.07 g, 60 mmol) of triethylamine in 25 mL of DMF at 0° C. was added dropwise, over 2 minutes, 3.34 mL (3.54 g, 44 mmol) of chloromethyl methyl ether. The mixture was allowed to come to room temperature and stirred for 16 hours. The mixture was partitioned between 50 mL of Et$_2$O and 50 mL of H$_2$O. The Et$_2$O layer was washed in succession with 50 mL of 5% HCl solution, 50 mL of pH 7 buffer and 50 mL of saturated NaCl solution. The Et$_2$O layer was concentrated in vacuo, and the residual oil was dissolved in 20 mL of THF and 2 mL of 6 N HCl solution. The mixture was stirred for 3 hours and partitioned between 50 mL of saturated NaCl solution and 50 mL of Et₂O. The Et₂O layer was dried (MgSO₄), filtered and concentrated to yield 1.53 g (56%) of 5d which was pure enough to use in the next step: ¹H NMR (CDCl₃) 3.33(s,2H), 3.38(s,3H), 4.72(s,2H), 10.01(brd s,1H).

In a similar manner, 2-methoxyethyl chloromethyl ether (4d) was reacted with mercaptoacetic acid to give S-(methoxyethoxy)methylmercaptoacetic acid (5d) in 58% yield as an oil.

Succinimidyl S-(1-ethoxyethyl)mercaptoacetate

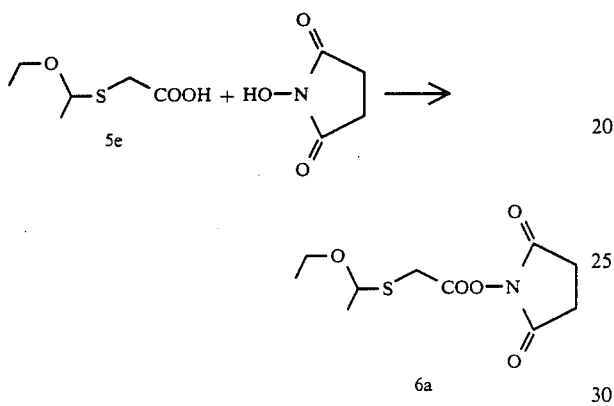

A solution of S-(1-ethoxyethyl)mercaptoacetic acid (5.76 g, 35.1 mmol) and N-hydroxysuccinimide (4.85 g, 42.1 mmol) was prepared in 100 mL of anhydrous THF. To this was added a solution of 1,3-dicycloherylcarbodiimide (8.70 g, 42.1 mmol) in 65 mL of anhydrous THF. The mixture was stirred at room temperature for 2 hours or until TLC analysis indicated complete formation of the succinimidyl ester. The mixture was then filtered, and the filtrate was concentrated in vacuo to a viscous residue. The residue was dissolved in ethyl acetate, washed with water, brine, and dried (MgSO₄). Removal of the solvent left the crude succinimidyl ester as an oil, which was further purified by flash chromatography on silica gel, using ethyl acetate-hexanes as the column eluent, to give 5.1 g of S-(1-ethoxyethyl)-mercaptoacetic acid succinimidyl ester as a colorless oil (56% yield): ¹H NMR (CDCl₃) 1.21(t,J=7.0 Hz,3H), 1.58(d,J=6.4 Hz,3H), 2.83(s,4H), 3.60(m,4H), 4.88(q,J=6.4 Hz,1H).

In a similar manner, compounds 6b-6e were prepared.

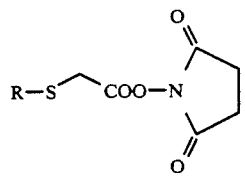

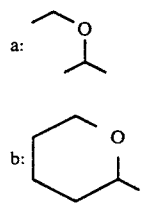

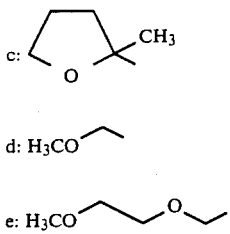

Synthesis of
4,5-Bis[S-(1-ethoxyethyl)thioacetamido]Pentanoic Acid

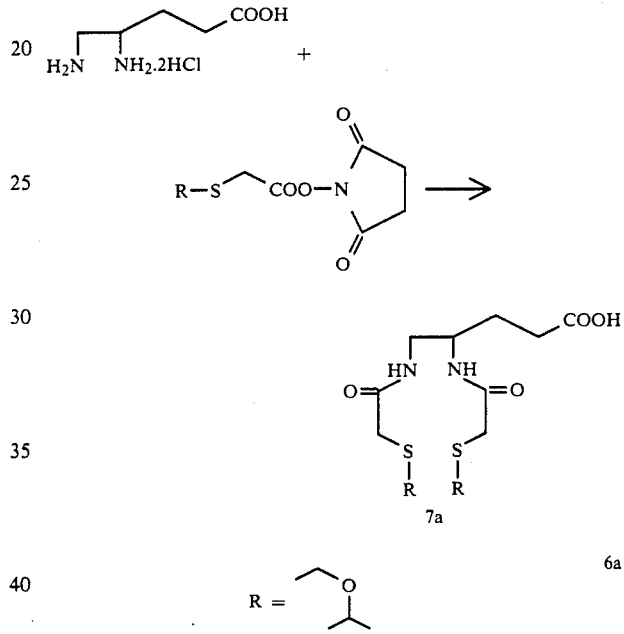

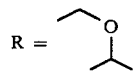

To a stirring suspension of 4,5-diaminopentanoic acid dihydrochloride (1.64 g, 8.0 mmol) in 32 mL of anhydrous dimethylformamide containing triethylamine (6.7 mL, 48.0 mmol) was added S-(1-ethoxyethyl)mercaptoacetic acid succinimidyl ester (4.60 g, 17.6 mmol) dissolved in 12 mL of anhydrous dimethylformamide. The reaction mixture was stirred at room temperature for 90 minutes or until TLC analysis indicated complete formation of 4,5-bis[S-(1-ethoxyethyl)thioacetamido] pentanoic acid. Then the reaction mixture was filtered, and the filtrate was concentrated to a viscous oil. The oil was dissolved in ethyl acetate and washed with successive portions of water until no N-hydroxysuccinimide was evident in the organic phase by TLC. The organic phase was washed with brine and dried (MgSO₄). Removal of solvent afforded 2.0 g of 4,5-bis[S(1-ethoxyethyl) thioacetamido]pentanoic acid as a viscous oil which solidified upon trituration with ether (59% yield): ¹H NMR (CDCl₃) 1.18(t,J=7.2 Hz, 6H), 1.53(d,J=6.6 Hz, 6H), 1.88(m,2H), 2.45(t,J=6.8 Hz, 2H), 3.30(s,4H), 3.55(m,6H), 4.10(m,1H), 4.77(q,J=6.6 Hz, 2H), 7.33(m,2H), 9.44(br,1H).

In a similar manner, compounds 7b and 7e were prepared.

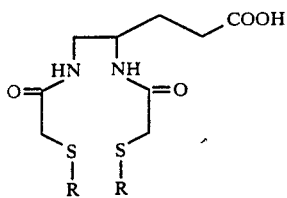

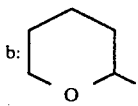
b:

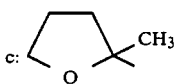
c:

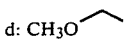
d: CH₃O

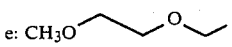
e: CH₃O

Synthetis of
2,3,5,6-tetrafluorophenyl-4,5-bis-[S-(1-ethoxyethyl)
thioacetamido]pentanoate

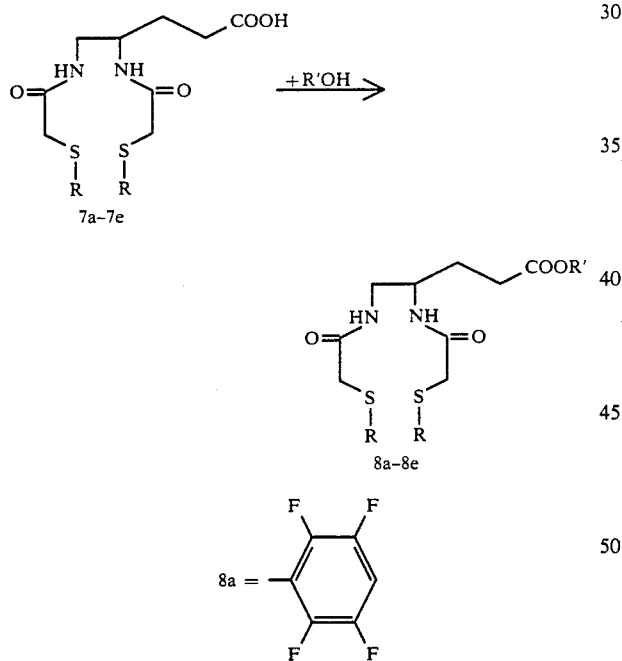

To a solution of 4,5-bis[S-(1-ethoxyethyl)thioacetamido]pentanoic acid (1.50 g, 3.53 mmol) and 2,3,5,6-tetrafluorophenol (0.88 g, 5.3 mmol) in 16 mL of anhydrous tetrahydrofuran was added 1,3-dicyclohexylcarbodiimide (0.95 g, 4.6 mmol) with rapid stirring. The mixture was stirred at room temperature for 18 to 24 hours or until TLC analysis indicated complete conversion to the ester. Then the mixture was filtered, and the filtrate was concentrated to give a solid. The solid was dissolved in a minimal amount of ethyl acetate and allowed to stand at 5° C. for 2 hours. The solution was then filtered to remove any precipitated dicyclohexylurea, and the filtrate was concentrated to afford solid 2,3,5,6-tetrafluorophenyl-4,5-bis[S-(1-ethoxyethyl) thioacetamido]pentanoate. The solid was washed with ether to remove any remaining 2,3,5,6-tetrafluorophenol. After drying in vacuo, 1.64 g of 2,3,5,6-tetrafluorophenyl-4,5-bis[S-(1- ethoxyethyl) thioacetamido]pentanoate was obtained (81% yield). $^1$H NMR (CDCl₃) 1.22(t,J=7.2 Hz,6H), 1.56(d,J=6.6 Hz,6H), 2.06(m,2H), 2.83(t,J=8 Hz,2H), 3.33(s,4H), 3.60(m,6H), 4.15(m,1H), 4.75(q,J=6.6 Hz,2H), 7.22(m,3H).

In a similar manner, the 2,3,5,6-tetrafluorophenyl esters of 7b-7e were prepared.

The 2-fluorophenyl (8a), 4-fluorophenyl (9a), 2,4-difluorophenyl (10), 2-pyrrolidone (11a), succinimidyl (12a), 2,3,5,6- tetrafluorothiophenyl (13a) esters were synthesized by the same method, except that the final purification was achieved by flash chromatography.

The N,N-diethylamino ester (14a) was prepared by the established isobutylchloroformate mixed anhydride method (The Peptides, Vol.1, Ch.6, Johannes Meinhofer, Academic Press, 1979 and "The Practice of Peptide Synthesis," *Reactivity and Structure: Concepts in Organic Chemistry*, Vol.21, pp.113-115, Springer-Verlog, 1984).

The cyanomethylester (15a) was also prepared by established method (The Peptides, Vol.1, Ch.6, Johannes Meinhofer, Academic Press, 1979 and The Practice of Peptide Synthesis, *Reactivity and Structure: Concepts in Organic Chemistry*, Vol.21, pp.109-110, Springer-Verlog, 1984).

Compound 16 was synthesized as follows:

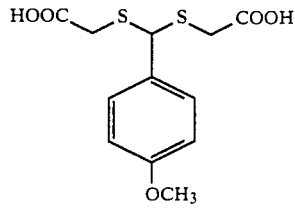

A solution of mercaptoacetic acid (13.9 mL, 200 mmol) and p-anisaldehyde (12.2 mL, 100 mmol) was prepared in 250 mL of dichloromethane. To this was slowly added boron trifluoride etherate (1.0 mL, 8.1 mmol) at room temperature with stirring. The reaction mixture was stirred at room temperature for 18 hours, at which point some of the product 16 had precipitated. Removal of the solvent left 16 as a white solid. The solid was collected and washed with portions of dichloromethane. Drying in vacuo left 19.1 g of 16 as a white solid (63% yield): $^1$H NMR (d₆DMSO) 3.24(s,2H), 3.30(s,2H), 3.72(s,3H), 5.24(s,1H), 6.82-7.41(m,4H), 10.40(b,2H).

Preparation of the bis-succinimidyl Ester (17)

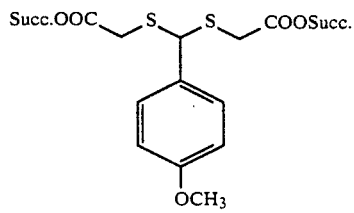

A solution of (4-methoxyphenyl)methanedithiol-S,S'-diacetic acid 16 (10.0 g, 33.1 mmole) and N-hydroxysuccinimide (8.37 g, 72.7 mmol) was prepared in 300 mL of anhydrous tetrahydrofuran. To this was added a solution of 1,3-dicyclohexylcarbodiimide (15.0 g, 72.7 mmole) in 128 mL of anhydrous tetrahydrofuran. After stirring at room temperature for about 24 hours, the reaction mixture was filtered to remove the dicyclohexylurea by-product of the reaction. Removal of the solvent from the filtrate left a white solid. Recrystallization from acetonitrile gave 10.24 g of bis-succinimidyl-(4-methoxyphenyl) methanedithio- S,S'-diacetate 17 (62% yield): $^1$H NMR (d$_6$DMSO) 2.84(s,8H), 3.74(m,7H), 5.42(s,1H), 7.18(m,4H).

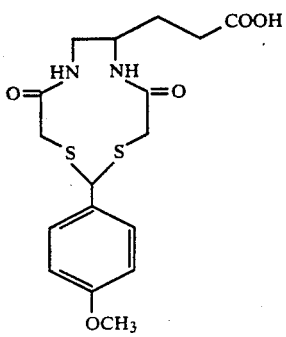

18

Preparation of (18)

A solution of 4,5-diaminopentanoic acid dihydrochloride (0.601 g, 2.93 mmol) in 580 mL of N,N-dimethylformamide and a solution of bis-succinimidyl-(4-methoxyphenyl) methanedithiol- S,S'-diacetate (1.46 g, 2.93 mmol) in 290 mL of N,N-dimethylformamide were added simultaneously and dropwise to a solution of triethylamine (0.82 mL, 5.88 mmol) in 290 mL of N,N-dimethylformamide with rapid stirring over a period of 30 minutes at room temperature. The mixture was then stirred for 4 hours. Removal of the solvent left an oil which was dissolved in ethyl acetate, washed with water and with brine, and dried (MgSO$_4$). Removal of the solvent left a solid. The solid was triturated with ether and collected by filtration. The solid was washed with ether and dried to give 0.91 g of 18 as a white solid (79% yield): $^1$H NMR (d$_6$-DMSO) 1.68(m,2H), 2.30(m,2H), 3.20(m,7H), 3.78(s,3H), 5.04(s,1H), 7.20(m,4H), 7.94(b,2H). MS(EI), m/e 398(M+), 380(M+-H$_2$O).

Preparation of 2,2-propanedithio-S,S'-diacetic Acid (19)

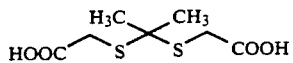

19

Acid-catalyzed condensation of 2-methoxypropene with mercaptoacetic acid by a method similar to the preparation of S-(1-ethoxyethyl)mercaptoacetic acid (5a) afforded 2,2-propanedithiol-S,S'-diacetic acid as a white crystalline solid in low yield: $^1$H NMR (d$_6$-DMSO) 1.54(s,3H), 3.38(s,2H).

O,O'-bis-succinimidyl(S,S'-isopropylidine)-S,S'-diacetic Acid (20)

To a solution of 897 mg (4.0 mmol) of 19 and 1.01 g (8.8 mmol) of N-hydroxysuccinimide in 20 mL of THF at 0° C. was added 1.81 g (8.8 mmol) of 1,3-dicyclohexylcarbodiimide. The mixture was stirred at 0° C. for 1 hour and at room temperature for 2 hours. The white solids were removed by vacuum filtration, and the filtrate was concentrated to a white solid which was allowed to stand in 20 mL of CH$_3$CN overnight. The solution was filtered again, and the filtrate was concentrated to give an oily solid. Recrystallization of the oily solid gave 1.22 g (73%) of a white solid: $^1$H NMR (CDCl$_3$) 1.74(s,6H), 2.89(s,8H), 3.75(s,4H).

S,S'-acetonyl-4,5-bis(thioacetamido) pentanoic acid (20)

To a solution of 205 mg (1 mmol) of 4,5-diaminobentanoic acid dihydrochloride and 557 ul (405 mg, 4 mmol) of Et$_3$N in 100 mL of DMF was added over 40 minutes a solution of 224 mg (1 mmol) of 19 in 100 mL of DMF. The mixture was stirred for 2 hours and concentrated to a viscous oil in vacuo. Purification by silica gel chromatography yielded an oil which was triturated with ether. The resulting white solid was collected by vacuum filtration to yield 68 mg (21%) of white powder: $^1$H NMR (CD$_3$OD) 1.78(s,6H), 1.62-2.00(m,2H), 2.14-2.63(m,2H), 3.29(s,4H), 3.00-3.50 (m,2H), 3.78-4.35(m,1H), 7.30-8.00(bid,2H).

EXAMPLE 2

Radiolabeling of a Chelating Compound of the Invention Comprising Ethoxyethyl Sulfur Protective Groups A chelating compound of the invention comprising ethoxyethyl sulfur protective groups on each of two sulfur atoms, and a 2,3,5,6-tetrafluorophenyl ester group (which may be reacted with a protein to form a conjugate) and having the following formula:

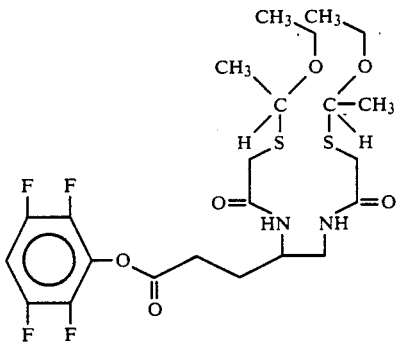

was radiolabeled with $^{99m}$Tc in accordance with a method of the invention.

One mL of sterile water for injection was added to a sterile vial containing a stannous gluconate complex (50 mg sodium gluconate and 1.2 mg stannous chloride dihydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 75-100 mCi, eluted from a $^{99}$Mo/$^{99}$Tc generator purchased from DuPont, Mediphysics, Mallinckrodt or E.R. Squibb) was added, and the vial was agitated gently to mix the contents, then incubated at room temperature for 10 minutes to form a $^{99m}$Tc-gluconate complex.

In an alternative procedure for providing the $^{99m}$Tc-gluconate exchange complex, the kit includes a vial containing a lyophilized preparation comprising 5 mg sodium gluconate, 0.12 mg stannous chloride dihydrate, about 0.1 mg gentisic acid as a stabilizer compound, and about 20 mg lactose as a filler compound. The amount of gentisic acid may vary, with the stabilizing effect, generally increasing up to about 0.1 mg. Interference with the desired reactions may occur when about 0.2 mg or more gentisic acid is added. The amount of lactose also may vary, with amounts between 20 and 100 mg, for example, being effective in aiding lyophilization. Addition of stabilizer and a filler compound is especially important when the vial contained these relatively small amounts of sodium gluconate and stannous chloride (compared to the alternative embodiment above). One mL of sodium pertechnetate (about 100 mCi) was added directly to the lyophilized preparation. The vial was agitated gently to mix the contents, then incubated as described above to form the $^{99m}$Tc-gluconate complex.

A separate vial containing 0.3 mg of a chelating agent in dry solid form was prepared by dispensing a solution of 0.3 mg chelating agent in acetonitrile into the vial, then removing the solvent under $N_2$ gas, and the resulting vial containing the chelating compound was provided in the kit. To this vial was then added 0.87 mL of 100% isopropyl alcohol, and the vial was gently shaken for about 2 minutes to completely dissolve the chelating agent, which was 2,3,5,6-tetrafluorophenyl 4,5-bis[S-(1-ethoxyethyl)thioacetamido]pentanoate. Next, 0.58 mL of this solution of the chelating agent was transferred to a vial containing 0.16 mL of glacial acetic acid/0.2 N HCl (2:14), and the vial was gently agitated. Of this acidified solution, 0.5 mL was transferred to the vial containing the $^{99m}$Tc-gluconate complex, prepared above. After gentle agitation to mix, the vial was incubated in a 75° C.+2° C. water bath for 15 minutes to form the chelate, then immediately transferred to a 0° C. ice bath for 2 minutes to stop the reaction. The resulting chelate was successfully conjugated to a monoclonal antibody through reaction of free amine groups on the antibody with the chelate's ester group, which had survived the radiolabeling procedure. The chelate had the following formula:

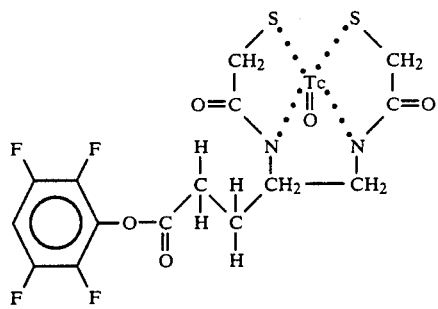

EXAMPLE 3

Radiolabeling of Various Chelating Compounds to Form $^{99m}$Tc Chelates

The radiolabeling procedure of Example 2 was repeated using chelating compounds of the invention having the following structures. The yields of the desired chelate (based on the percentage of $^{99m}$TcO$_4^-$ added to each reaction mixture which became chelated) are presented.

1. A chelating compound comprising two sulfur atoms, an active ester, and a p-anisylidine thioacetal sulfur protective group:

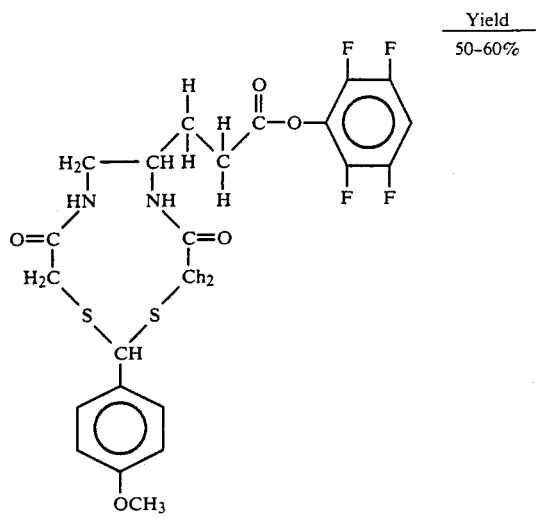

2. A chelating compound comprising two sulfur atoms, an active ester, and an acetonyl thioacetal sulfur protective group:

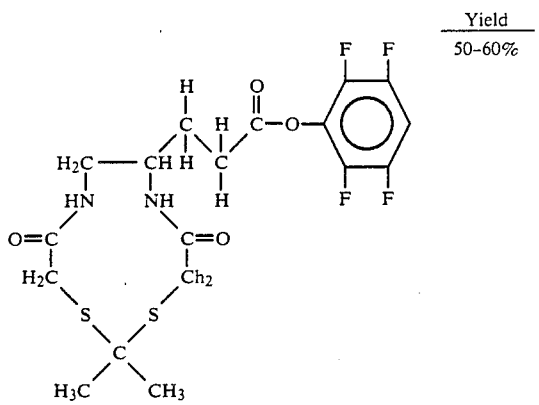

3. A chelating compound comprising two sulfur atoms, an active ester, and a tetrahydropyranyl hemithioacetal sulfur protective group:

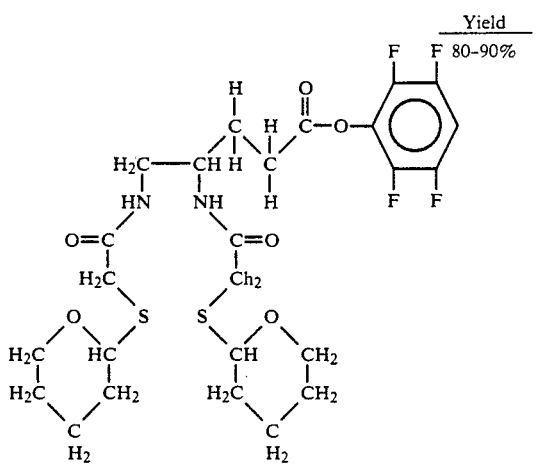

4. A chelating compound comprising one sulfur atom, an active ester, and a tetrahydropyranyl hemithioacetal sulfur protective group:

Yield
98-100%

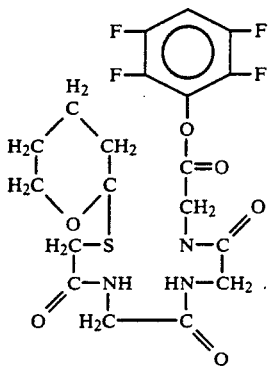

5. A chelating compound comprising two sulfur atoms, an active ester, and an ethoxyethyl hemithioacetal sulfur protective group:

Yield
82-85%

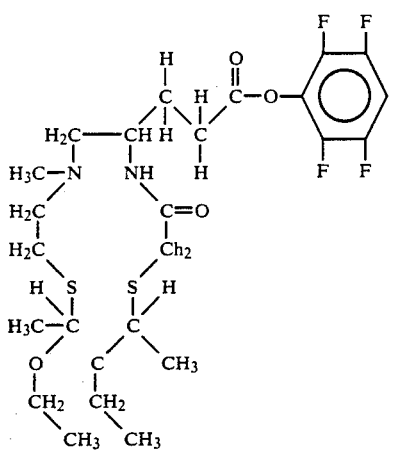

6. The same chelating compound structure as in (5), but with an ethoxyethyl protective group on one sulfur and a benzoyl protective group

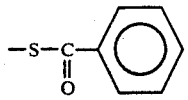

on the other sulfur. The yield was 90%.

EXAMPLE 4

Preparation of 188Re-Labeled Chelate

Sodium perrhenate (3 mL, 15 mCi, produced from a W-188/Re-188 research scale generator) was added to a vial containing a lyophilized mixture comprising citric acid, 75 mg; stannous chloride, 0.75 mg; gentisic acid, 0.25 mg; and lactose, 100 mg. The vial was agitated gently to mix the contents, then incubated at room temperature for 10 minutes to form a $^{188}$Re-citrate exchange complex. To a separate vial containing 0.50 mg of 2,3,5,6-tetrafluorophenyl-4,5-bis[S-(1-ethoxyethyl) thioacetamido]pentanoate (the chelating compound shown in Example 2), 0.50 mL of isopropyl alcohol was added and the vial was agitated for 2 minutes to completely dissolve the chelating agent. Next, 0.30 mL of this solution was transferred to the vial containing the $^{188}$Re- citrate complex prepared above. After gentle mixing, the vial was incubated in a 75° ±+2 C water bath for 15 minutes, then immediately transferred to a 0° C. ice bath for 2 minutes. The yields of $^{188}$Re-labeled chelate then ranged between 75% and 90% as measured by reversed phase $C_{18}$ HPLC analysis.

A column containing a $C_{18}$ reversed phase low-pressure material (Baker $C_{18}$ cartridges) was used to purify the $^{188}$Re- labeled chelate. After conditioning of the cartridge with ethanol and water, the sample was loaded and washed with three times 2 mL of water and three times 2 mL of 20% ethanol/0.01 M phosphate buffer. The column was then dried in vacuo and eluted with two times 1.0 mL acetonitrile. About 75% of the $^{188}$Re- radioactivity was recovered in greater than 95% purity as the ester chelate compound. The organic solvent was then evaporated under a flow of inert gas.

EXAMPLE 5

Monosaccharide Sulfur-Protecting Groups

Monosaccharide derivatives comprising five or six carbon atoms are attached to sulfur donor atoms as protecting groups.

D-glucose is reacted as described by Tulshian and Fraser-Reid (*J. Amer. Chem. Soc.*, 103, 474, 1981), then as described by Fraser-Reid and Radatus (*J. Amer. Chem. Soc.*, 92, 5288, 1970) to produce a 6'-deoxy-diacetyl glucal compound:

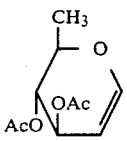

Compound 20

D-galactose is derivatized using the same procedures, thereby producing a 6'-deoxy-diacetyl galactal compound:

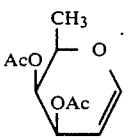

Compound 21

L-rhamnose is derivatized as described in U.S. Pat. No. 4,427,664 to produce a diacetyl rhamnal compound:

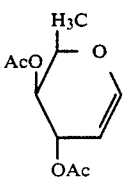

Compound 22

D-xylose is reacted as described by Helfreich and Ost (*Chem. Ber.*, 95, 2612, 1962) to produce a triacetyl-xylopyranosyl bromide compound:

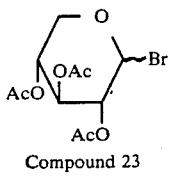

Compound 23

Compounds 20 through 23 then are reacted with mercaptoacetic acid (HS—CH$_2$—COOH) in the presence of p-toluene-sulfonic acid monohydrate catalyst and methylene chloride. The reaction is generally as described in Example 1 for the reaction of various compounds with mercaptoacetic acid, and the following derivatives are produced by the reactions:

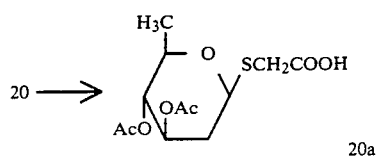

20a

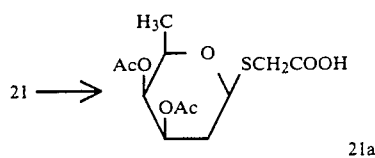

21a

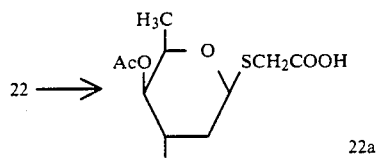

22a

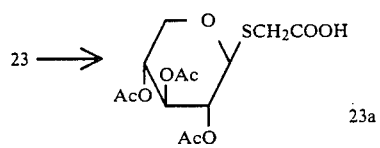

23a

Each of compounds 20a-23a is reacted with N-hydroxysuccinimide in the presence of 1,3-dicyclohexyl carbodiimide (both in anhydrous THF) to produce the succinimidyl ester of each compound. The reactions are conducted generally as described for the production of compounds 6a-6e in example 1 above. The resulting succinimidyl ester compounds are represented by the following formula:

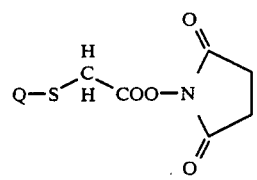

Wherein Q represents the ring portion of each compound.

The succinimidyl ester compounds are reacted with 4,5-diaminopentanoic acid dihydrochloride in anhydrous dimethylformamide containing triethylamine. The reaction is generally as described for the synthesis of compound 7a in example 1.

When the chelating compound is to be attached to a protein, a protein conjugation group (e.g., an active ester such as a tetrafluorophenyl ester) may be attached as described in example 1 or by any other suitable procedure.

The acetate protecting groups are removed from the compounds and replaced by hydroxyls by treatment with sodium methoxide (or another base) and methanol.

The resulting chelating compounds are represented by the following formula:

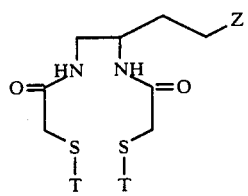

wherein Z represents a protein conjugation group (e.g., a tetrafluorophenyl ester group) and each T represents a sulfur protecting group derived from a monosaccharide. The two T groups generally are the same and each T group is selected from one of the following protecting groups (wherein the sulfur donor atom of the chelating compound to which the protecting group is bonded also is shown):

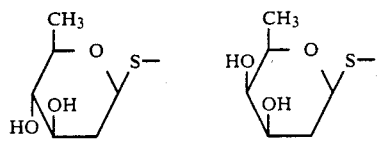

Derived from D-Glucose

Derived from D-Galactose

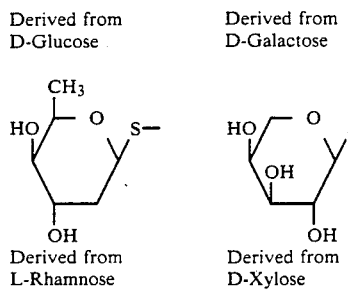

Derived from L-Rhamnose

Derived from D-Xylose

One such chelating compound in which the sulfur protecting groups are derived from glucose is the N$_2$S$_2$ chelating compound of the following formula:

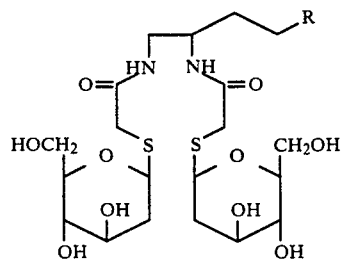

wherein R represents a protein conjugation group such as a carboxylic ester (e.g., a 2,3,5,6-tetrafluorophenyl ester).

What is claimed is:

1. A method of producing a radionuclide metal chelate, comprising reacting a radionuclide metal with a chelating compound under conditions of acidic pH, thereby producing said radionuclide metal chelate, wherein said chelating compound comprises one or more sulfur donor atoms attached to a protecting group, and said protecting group, when taken together with the one or more sulfur donor atoms attached thereto, is a hemithioacetal group or a thioacetal group.

2. The method of claim 1, wherein the chelating compound comprises two sulfur donor atoms which, when taken together with a protecting group attached thereto, define a thioacetal group of the formula:

$$\begin{array}{c} R^1 \quad R^2 \\ \diagdown C \diagup \\ \diagup \quad \diagdown \\ S \quad S \\ \diagdown \quad \diagup \end{array}$$

wherein $R^1$ and $R^2$ are independently selected from the group consisting of hydrogen; lower alkyl groups; and an aromatic ring having an electron donating group bonded directly to said aromatic ring.

3. The method according to claim 2 wherein said electron donating group is selected from the group consisting of a methoxy group, an ethoxy group, and a hydroxy group.

4. The method according to claim 3 wherein said electron donating group is a methoxy group and said thioacetal group is represented by the formula:

[structure: para-methoxyphenyl CH with two S substituents]

5. The method according to claim 2, wherein $R^1$ and $R^2$ are both methyl groups.

6. The method of claim 1 wherein the chelating compound comprises at least one sulfur donor atom which, when taken together with the protecting group attached thereto, defines a hemithioacetal group of the formula:

$$\begin{array}{c} OR^3 \\ | \\ R^4-C-R^5 \\ | \\ S \\ | \end{array}$$

wherein $R^3$ and $R^4$ each represent a lower alkyl group, and $R^5$ represents hydrogen or a lower alkyl group.

7. The method of claim 6, wherein said protecting group is an ethoxyethyl group.

8. The method of claim 1 wherein the chelating compound comprises at least one sulfur donor atom which, when taken together with the protecting group attached thereto, defines a hemithioacetal group of the formula:

$$\begin{array}{c} OR^3 \\ | \\ R^4-C-R^5 \\ | \\ S \\ | \end{array}$$

wherein $R^3$ and $R^4$ are taken together with the carbon atom and the oxygen atom shown in said formula to define a nonaromatic ring, and $R^5$ represents hydrogen or a lower alkyl group.

9. The method of claim 8, wherein said protecting group is selected from the group consisting of tetrahydropyranyl, 2-methyl tetrahydropyranyl, tetrahydrofuranyl and 2-methyl tetrahydrofuranyl groups.

10. The method of claim 8 wherein said protecting group is derived from a monosaccharide.

11. The method of claim 10 wherein the hemithioacetal group is selected from the group consisting of:

[four monosaccharide-derived hemithioacetal structures]

12. The method of claim 1, wherein the chelating compound comprises at least one sulfur donor atom which, when taken together with the protecting group attached thereto, defines a hemithioacetal group having one of the following formulae:

—S—CH$_2$—O—CH$_2$—CH(CH$_3$)$_2$

—SCH$_2$OCH$_3$

—S—CH$_2$—O—(CH$_2$)$_2$—OCH$_3$

13. The method of claim 1, 2, 6, 8, 10, or 12 wherein the chelating compound additionally comprises a base labile group.

14. The method of claim 13 wherein the base labile group is a protein conjugation group.

15. The method of claim 14 wherein the protein conjugation group is selected from the group consisting of isothiocyanates, esters, maleimides, and other Michael-type acceptor groups.

16. The method of claim 1, wherein the chelating compound comprises two nitrogen donor atoms and at least two sulfur donor atoms.

17. The method of claim 1, wherein the chelating compound comprises three nitrogen donor atoms and one sulfur donor atom, wherein the sulfur donor atom, when taken together with the protecting group attached thereto, is a hemithioacetal group.

18. The method of claim 16 or 17, wherein each of said sulfur donor atoms has a protecting group derived from a monosaccharide attached thereto.

19. The method of claim 1, 16, or 17, wherein said metal radionuclide is selected from radioisotopes of technetium, rhenium, lead, palladium, bismuth, and copper.

20. The method of claim 19 wherein the metal radionuclide is selected from radioisotopes of technetium or rhenium and is in the form of an exchange complex when reacted with the chelating compound.

* * * * *